United States Patent
Hanasaki et al.

(10) Patent No.: US 6,967,200 B2
(45) Date of Patent: *Nov. 22, 2005

(54) REMEDIES FOR CIRRHOSIS

(75) Inventors: Kohji Hanasaki, Osaka (JP); Minoru Ikeda, Osaka (JP); Takashi Ono, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 138 days.

This patent is subject to a terminal disclaimer.

(21) Appl. No.: 10/312,366

(22) PCT Filed: Jun. 27, 2001

(86) PCT No.: PCT/JP01/05481

§ 371 (c)(1),
(2), (4) Date: Dec. 26, 2002

(87) PCT Pub. No.: WO02/00256

PCT Pub. Date: Jan. 3, 2002

(65) Prior Publication Data

US 2004/0106669 A1 Jun. 3, 2004

(30) Foreign Application Priority Data

Jun. 29, 2000 (JP) ........................................ 2000-195436

(51) Int. Cl.$^7$ ........................ A61K 31/50; A61K 31/44; A61K 31/40
(52) U.S. Cl. ........................ 514/249; 514/299; 514/411
(58) Field of Search ................................ 514/249, 299, 514/411

(56) References Cited

U.S. PATENT DOCUMENTS 5,478,857 A    12/1995   Clemens et al. ............ 514/381

FOREIGN PATENT DOCUMENTS

| EP | 0 620 214 | 10/1994 |
| EP | 0 620 215 | 10/1994 |
| EP | 0 675 110 | 10/1995 |
| EP | 0 952 149 | 10/1999 |
| EP | 1 085 021 | 3/2001 |
| WO | 96/03120 | 2/1996 |
| WO | 96/03376 | 2/1996 |
| WO | 96/03383 | 2/1996 |
| WO | 97/21664 | 6/1997 |
| WO | 97/21716 | 6/1997 |
| WO | 98/18464 | 5/1998 |
| WO | 98/24437 | 6/1998 |
| WO | 98/24756 | 6/1998 |
| WO | 98/24794 | 6/1998 |
| WO | 98/25609 | 6/1998 |
| WO | 99/51605 | 10/1999 |
| WO | 99/59999 | 11/1999 |
| WO | 01/26653 | 4/2001 |

OTHER PUBLICATIONS

Design of Prodrugs, Hans Bundgaard, pp. 7–9 and 21–24, Elsevier, Amsterdam 1985.
S. Berge et al., "Journal of Pharmaceutical Sciences", vol. 66, No. 1, pp. 1–19, Jan. 1977.
L. Cupillard et al., "Cloning, Chromosomal Mapping, and Expression of a Novel Human Secretory Phospholipase $A_2$", The Journal of Biological Chemistry, vol. 272, No. 25, pp. 15745–15752, Jun. 20, 1997.
L. Reynolds et al., "Analysis of Human Synovial Fluid Phospholipase $A_2$ on Short Chain Phosphatidylcholine-Mixed Micelles: Development of a Spectrophotometric Assay Suitable for a Microtiterplate Reader", Analytical Biochemistry, vol. 204, pp. 190–197, 1992.
Kohji Hanasaki et al., "Purified Group X Secretory Phospholipase $A_2$ Induced Prominent Release of Arachidonic Acid from Human Myeloid Leukemia Cells", The Journal of Biological Chemistry, vol. 274, No. 48, pp. 34203–34211, Nov. 26, 1999.
M. Murakami et al., "Different Functional Aspects of the Group II Subfamily (Types IIA and V) and Type X Secretory Phospholipase $A_2$ in Regulating Arachidonic Acid Release and Prostaglandin Generation", The Journal of Biological Chemistry, vol. 274, No. 44, pp. 31435–31444, Oct. 29, 1999.

*Primary Examiner*—Raymond J. Henley, III
(74) *Attorney, Agent, or Firm*—Wenderoth, Lind & Ponack, L.L.P.

(57) ABSTRACT

It is provided that type-X $sPLA_2$ inhibitors are useful in preventing or treating hepatocirrhosis.

11 Claims, No Drawings

REMEDIES FOR CIRRHOSIS

This application is a U.S. national stage of International Application No. PCT/JP01/05481 filed Jun. 27, 2001.

TECHNICAL FIELD

The present invention relates to a composition for the prevention or treatment of hepatocirrhosis which contains an inhibitor against type-X sPLA$_2$ (secretary PLA$_2$) as an active ingredient.

BACKGROUND ART sPLA$_2$ inhibitors are disclosed in EP-620214 (JP Laid-Open (Tokukai) No. 95/010838, U.S. Pat. No. 5,578,634). And it is described in U.S. Pat. No. 5,478,857 (WO95/17183, JP Laid-Open (Tokuhyo) No. 97/507069) that type-II sPLA$_2$ inhibitors are effective for apoptosis associated disease. However, the above-mentioned documents do not describe compounds having inhibitory activities against type-X sPLA$_2$ or that type-X sPLA$_2$ inhibitors are effective for the treatment of hepatocirrhosis.

DISCLOSURE OF INVENTION

The inventors of the present invention examined the expression of type-X sPLA$_2$ in various kinds of human pathological tissues with anti-type-X sPLA$_2$ antibody. They found the elevated expression of type-X sPLA$_2$ in pseudolobule in the liver prepared from patients of hepatocirrhosis.

The immunohistochemical analysis of each tissue was performed as follows. At first, anti-human type-X sPLA$_2$ antibody was added to the slides prepared from normal adult liver tissues or liver tissues prepared from patients of hepatocirrhosis and incubated for several hours. Next, in order to examine the expression of type-X sPLA$_2$ in the tissues, the expression of type-X sPLA$_2$ was visualized by using the methods such as the immunohistochemical labeling to detect the type-X sPLA$_2$ signals. Consequently, the type-X sPLA$_2$ signals were detected in the slides prepared from liver tissues prepared from patients of hepatocirrhosis, suggesting that the expression of type-X sPLA$_2$ is elevated in liver tissues prepared from patients of hepatocirrhosis.

In addition, the inventors of the present invention performed the experiments for neutralization of type-X sPLA$_2$ signals. Precisely, before the addition of anti-human type-X sPLA$_2$ antibody to the slides, the slides were incubated with the purified type-X sPLA$_2$ protein for several hours. Hereafter, the slides were processed as the same procedures as described above to examine the type-X sPLA$_2$ signals. Consequently, the type-X sPLA$_2$ signals were disappeared in the slides prepared from liver tissues.

Thus, the elevated expression of type-X sPLA$_2$ was confirmed in liver tissues prepared from patients of hepatocirrhosis and the inventors of the present invention achieved the following present invention.

That is to say, the present invention relates to I) a composition for prevention or treatment of hepatocirrhosis which contains a type-X sPLA$_2$ inhibitor as an active ingredient.

In more detail, the present invention relates to the following II) to XIII).

II) A composition for prevention or treatment of hepatocirrhosis which contains as an active ingredient a compound represented by the formula (I):

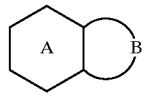

(I)

wherein Ring A is represented by the formula (a) to (d):

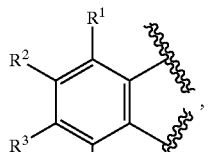

(a)

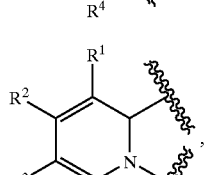

(b)

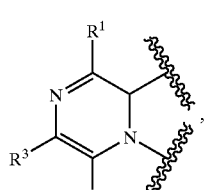

(c)

or

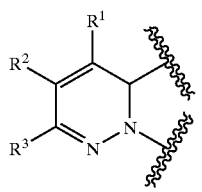

(d)

wherein $R^1$ and $R^2$ are each independently hydrogen atom, non-interfering substituent, or -($L^1$)-(acidic group) wherein $L^1$ is an acid linker having an acid linker length of 1 to 5, provided that one of the $R^1$ and $R^2$ is -($L^1$)-(acidic group);

$R^3$ and $R^4$ are each independently hydrogen atom, non-interfering substituent, carbocyclic group, carbocyclic group substituted with a non-interfering substituent(s), heterocyclic group, or heterocyclic group substituted by a non-interfering substituent(s); and —B— is represented by the formula (e) to (h):

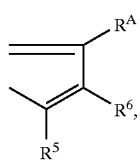

(e)

-continued (f)
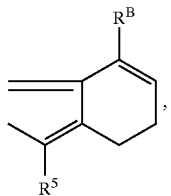

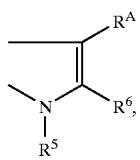

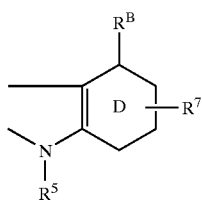

wherein $R^5$ is (j) C1 to C20 alkyl, C2 to C20 alkenyl, C2 to C20 alkynyl, carbocyclic group, or heterocyclic group, (k) the group represented by (j) each substituted independently with at least one group selected from non-interfering substituents, or $-(L^2)-R^8$ wherein $L^2$ is a divalent linking group of 1 to 18 atom(s) selected from hydrogen atom(s), nitrogen atom(s), carbon atom(s), oxygen atom(s), and sulfur atom(s), and $R^8$ is a group selected from the groups (j) and (k);

$R^6$ is hydrogen atom, halogen, C1 to C3 alkyl, C3 to C4 cycloalkyl, C3 to C4 cycloalkenyl, C1 to C3 alkyloxy, or C1 to C3 alkylthio;

$R^7$ is hydrogen atom or non-interfering substituent;

$R^A$ is represented by the formula:

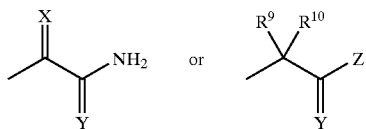

wherein $R^9$ and $R^{10}$ are each independently hydrogen atom, C1 to C3 alkyl, or halogen;

X and Y are each independently oxygen atom or sulfur atom; and

Z is $-NH_2$ or $-NHNH_2$;

$R^B$ is $-CONH_2$ or $-CONHNH_2$; and,

Ring D is cyclohexene ring or benzene ring;

provided that Ring A is (b), (c), or (d) when —B— is (e) or (f), a prodrug thereof, its pharmaceutically acceptable salt, or its solvate.

III) A composition for prevention or treatment of hepatocirrhosis which contains a compound, a prodrug thereof, its pharmaceutically acceptable salt, or its solvate as described in II) as an active ingredient, wherein $R^1$ is hydrogen atom or $-(L^3)-R^{11}$ wherein $L^3$ is $-OCH_2-$, $-SCH_2-$, $-NH-CH_2-$, $-CH_2-CH_2-$, $-O-CH(CH_3)-$, or $-O-CH(CH_2CH_2C_6H_5)-$; $R^{11}$ is $-COOH, -CONHSO_2C_6H_5, -SO_3H,$ or $-P(O)(OH)_2$; and $R^2$ is hydrogen atom or $-(L^4)-R^{12}$ wherein $L^4$ is represented by the formula:

(g)

(h)

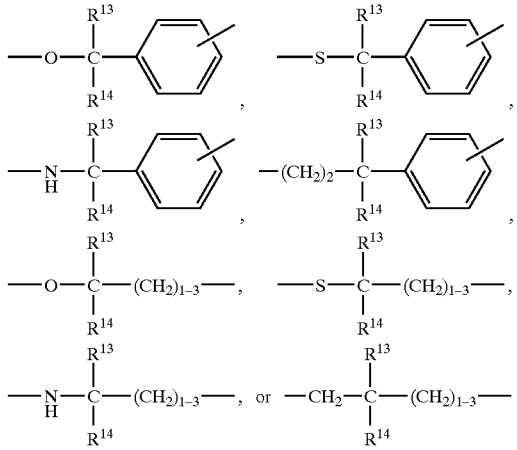

wherein $R^{13}$ and $R^{14}$ are each independently hydrogen atom, C1 to C10 alkyl, C1 to C10 aralkyl, carboxy, alkyloxycarbonyl, or halogen; $R^{12}$ is $-COOH, -SO_3H,$ or $-P(O)(OH)_2$, provided $R^1$ and $R^2$ are not hydrogen atom at the same time.

IV) A composition for prevention or treatment of hepatocirrhosis which contains a compound, a prodrug thereof, its pharmaceutically acceptable salt, or its solvate as described in II) or III) as an active ingredient, wherein $R^3$ is hydrogen atom, C1 to C6 alkyl, C3 to C6 cycloalkyl, aryl, or a heterocyclic group and $R^4$ is hydrogen atom or halogen.

V) A composition for prevention or treatment of hepatocirrhosis which contains a compound, a prodrug thereof, its pharmaceutically acceptable salt, or its solvate as described in any one of II) to IV) as an active ingredient, wherein $R^5$ is $-(CH_2)_{1-6}-R^{15}$ wherein $R^{15}$ is represented by the formula:

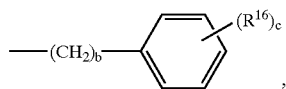

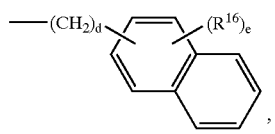

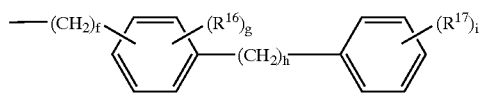

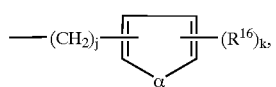

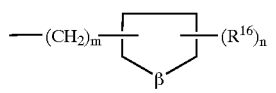

-continued

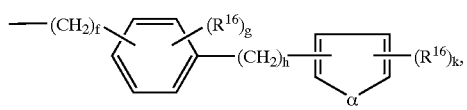

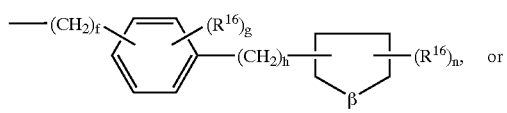

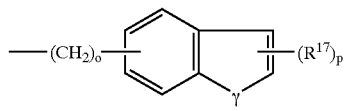

wherein b, d, f, h, j, m, and o are independently an integer from 0 to 2; $R^{16}$ and $R^{17}$ are each independently halogen, C1 to C10 alkyl, C1 to C10 alkyloxy, C1 to C10 alkylthio, aryloxy, or C1 to C10 haloalkyl; α is oxygen atom or sulfur atom; β is —CH$_2$— or —(CH$_2$)$_2$—; γ is oxygen atom or sulfur atom; c, i, and p are independently an integer from 0 to 5; e is an integer from 0 to 7; g is an integer from 0 to 4; k and n are each independently an integer from 0 to 3.

VI) A composition for prevention or treatment of hepatocirrhosis which contains a compound, a prodrug thereof, its pharmaceutically acceptable salt, or its solvate as described in V) as an active ingredient, wherein $R^5$ is —CH$_2$—$R^{18}$ wherein $R^{18}$ is represented by the formula:

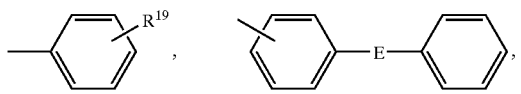

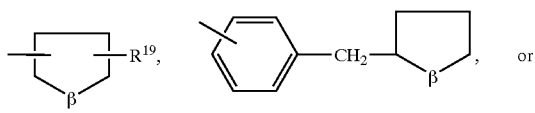

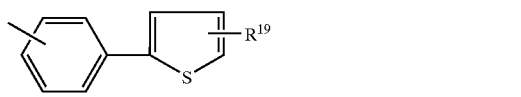

wherein β is —CH$_2$— or —(CH$_2$)$_2$—; $R^{19}$ is hydrogen atom, C1 to C3 alkyl, or halogen; E is a bond, —CH$_2$— or —O—.

VII) A composition for prevention or treatment of hepatocirrhosis which contains a compound, a prodrug thereof, its pharmaceutically acceptable salt, or its solvate as described in any one of II) to VI) as an active ingredient, wherein $R^1$ is —OCH$_2$COOH.

VIII) A composition for prevention or treatment of hepatocirrhosis which contains a compound, a prodrug thereof, its pharmaceutically acceptable salt, or its solvate as described in any one of II) to VII) as an active ingredient, wherein $R^2$ is hydrogen atom.

IX) A composition for prevention or treatment of hepatocirrhosis which contains a compound, a prodrug thereof, its pharmaceutically acceptable salt, or its solvate as described in any one of II) to VIII) as an active ingredient, wherein $R^6$ is C1 to C3 alkyl.

X) A composition for prevention or treatment of hepatocirrhosis which contains a compound, a prodrug thereof, its pharmaceutically acceptable salt, or its solvate as described in any one of II) to IX) as an active ingredient, wherein $R^A$ is —CH$_2$CONH$_2$ or —COCONH$_2$.

XI) A composition for prevention or treatment of hepatocirrhosis which contains a compound as an active ingredient represented by the formula:

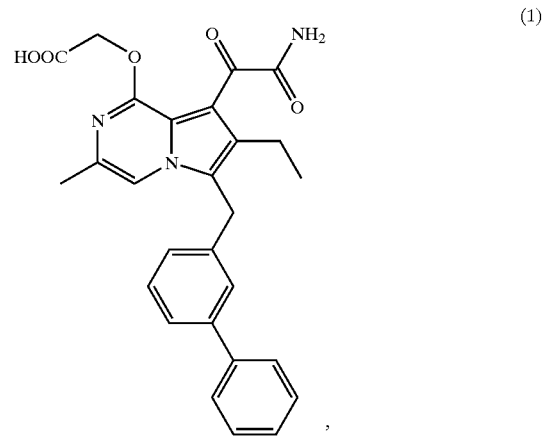

(1)

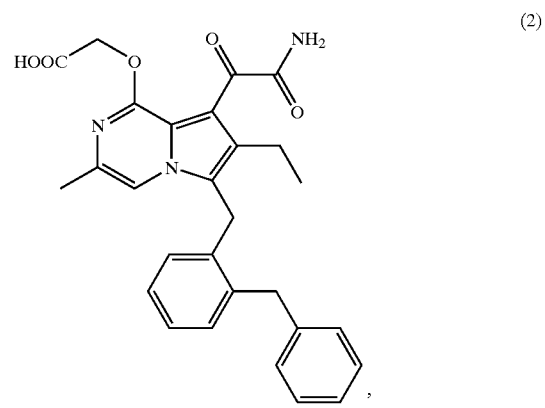

(2)

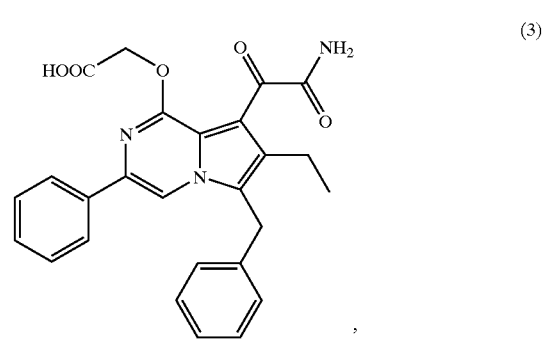

(3)

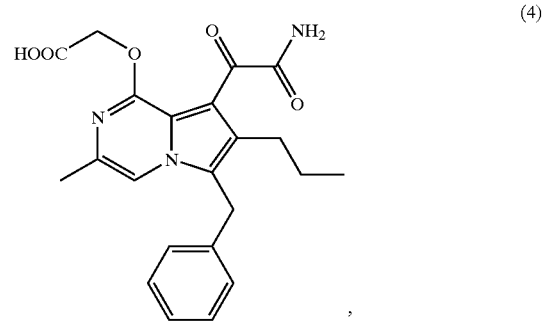

(4)

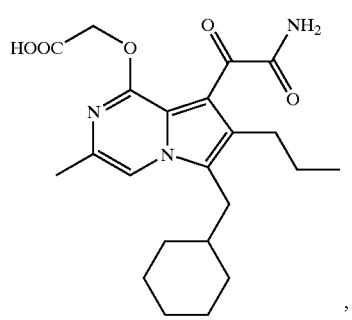
(5)
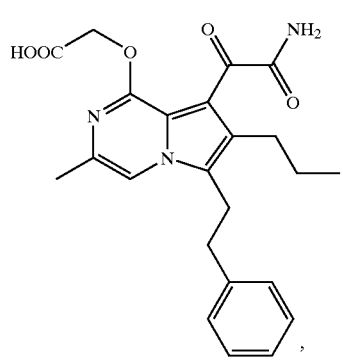
(6)
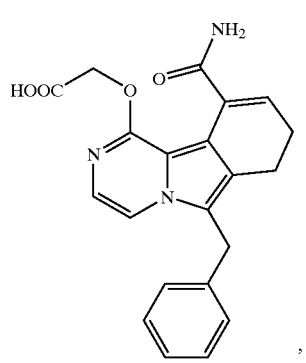
(7)
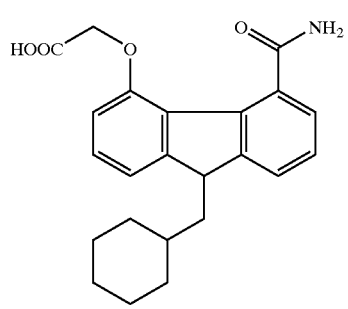
(8)
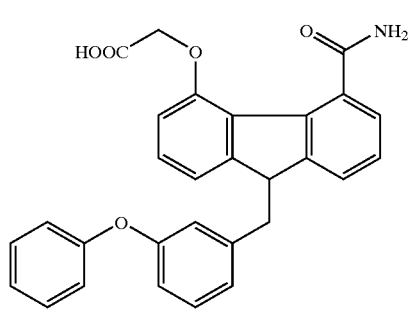
(9)
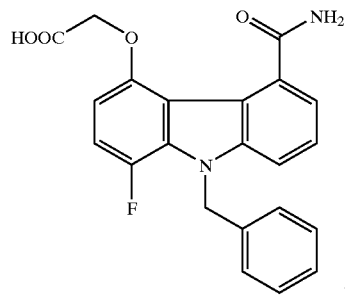
(10)
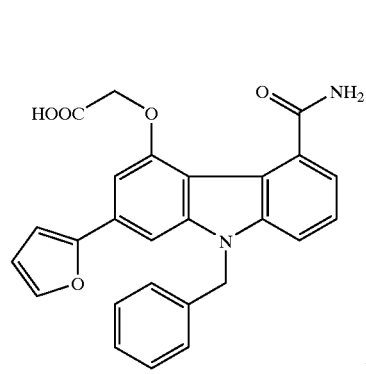
(11)
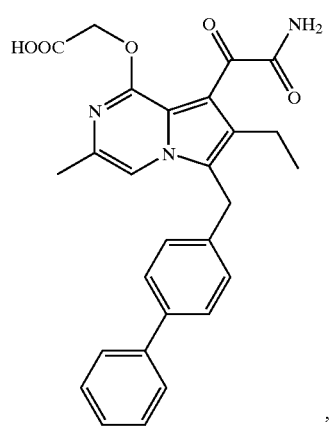
(12)
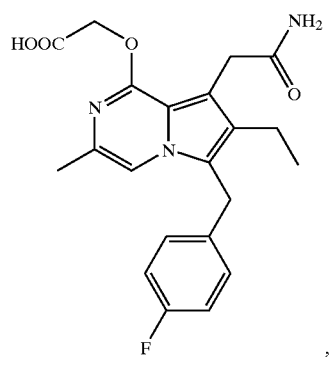
(13)

a prodrug thereof, its pharmaceutically acceptable salt, or its solvate.

XII) Use of a type-X sPLA$_2$ inhibitor for the preparation of a medicament for the treatment of hepatocirrhosis.

XIII) Use as described in XII) wherein the type-X sPLA$_2$ inhibitor is the compound described in any one of II) to XI).

XIV) A method of treating a mammal, including a human, to alleviate the pathological effects of hepatocirrhosis, which comprises administration to said mammal of a type-X sPLA$_2$ inhibitor in a pharmaceutically effective amount.

XV) A method as described in XIV) wherein the type-X sPLA$_2$ inhibitor is the compound described in any one of II) to XI).

The Present Invention is Illustrated in Detail as Follows

Type-X sPLA$_2$ inhibitors mean compounds which have an inhibitory activity against type-X sPLA$_2$ and other optional activities such as inhibitory activities against other enzymes or affinities for any receptors. Namely, the inhibitors include any compound having stronger activities against type-X sPLA$_2$ than that having no such activities in the evaluation test therefore. Especially, type-X sPLA$_2$ selective inhibitors are preferred as type-X sPLA$_2$ inhibitors of the present invention. For example, compounds whose IC$_{50}$ values against type-X sPLA$_2$ are 1 μM or less in the experiment of Example 2 are preferred. Compounds having IC$_{50}$ values 100 nM or less are more preferred.

A compound having type-X sPLA$_2$ inhibitory activities, having one or more of chiral center(s), may exist as an optically active member. Likewise, a compound containing alkenyl or alkenylene, may be a cis- or trans-isomer. Mixtures of R- and S-isomers as well as of cis- and trans-isomers, and mixtures of R- and S-isomers containing a racemic mixture are included in the scope of the present invention. An asymmetric carbon atom may exist also in a substituent such as alkyl group. All such isomers and mixtures are included in the present invention. A specified stereoisomer can be manufactured by subjecting to stereospecific reaction well known to those skilled in the art applying a previously separated starting material having an asymmetrical center or by preparing a mixture of stereoisomers and separating the mixture in accordance with a well-known manner.

Prodrug is a derivative of a compound with type-X sPLA$_2$ inhibitory activities, having a group which can be decomposed chemically or metabolically, and becoming pharmaceutically active by solvolysis or in vivo under a physiological condition. Although the derivative, acid derivative or basic derivative, exhibits activity, an acid derivative is more advantageous in solubility, tissue affinity, and release control in mammal organism (Bungard, H., Design of Prodrugs, pp. 7–9, 21–24, Elsevier, Amsterdam, 1985). For instance, prodrugs, including an acid derivative such as an ester which is prepared by reacting a basal acid compound with a suitable alcohol, or an amide which is prepared by reacting a basal acid compound with a suitable amine, are well known to those skilled in the art. Simple aliphatic or aromatic esters derived from acid groups contained in the compounds according to the present invention are preferable prodrugs. Particularly preferred esters as prodrugs are C1–C6 alkylester (e.g. methyl ester, ethyl ester). Double ester such as (acyloxy)alkyl ester or ((alkyloxycarbonyl)oxy)-alkyl ester type prodrugs may be optionally manufactured.

When a compound having type-X sPLA$_2$ inhibitory activities has an acidic or basic functional group, a variety of salts having a higher water solubility and more physiologically suitable properties than those of the original compound can be formed. An example of typical pharmaceutically acceptable salts includes salts with alkali metal and alkaline earth metal such as lithium, sodium, potassium, magnesium, aluminum and the like, but it is to be noted that such pharmaceutically acceptable salts are not limited thereto. A salt is easily manufactured from a free acid by either treating an acid in a solution with a base, or allowing an acid to be in contact with an ion exchange resin. Addition salts of the compounds having type-X sPLA$_2$ inhibitory activities with relatively non-toxic inorganic bases and organic bases, for example, amine cation, ammonium, and quaternary ammonium derived from nitrogenous bases having a basicity sufficient for forming a salt of the compounds of the present invention are included in the definition of "pharmaceutically acceptable salts". (e.g., S. M. Berge et al., "Pharmaceutical Salts," J. Phar. Sci., 66, 1–19 (1977)). Furthermore, basic groups of a compound having type-X sPLA$_2$ inhibitory activities are reacted with a suitable organic or inorganic acid to form salts such as acetates, benzenesulfonates, benzoates, bicarbonates, bisulfates, bitartrates, borates, bromides, camsylates, carbonates, chlorides, clavulanates, citrates, edetates, edisylates, estolates, esylates, fluorides, fumarates, gluceptates, gluconates, glutamates, glycolylarsanilates, hexylresorcinates, hydroxynaphthoates, iodides, isothionates, lactates, lactobionates, laurates, malates, maleates, mandelates, mesylates, methylbromides, methylnitrates, methylsulfates, mucates, napsylates, nitrates, oleates, oxalates, palmitates, pantothenates, phosphates, polygalacturonates, salicylates, stearates, subacetates, succinates, tannates, tartrates, tosylates, trifluoroacetates, trifluoromethanesulfonates, valerates and the like.

The solvate includes solvates with organic solvents and/or hydrates. In case of forming a hydrate, a questioned compound may be coordinated with a suitable number of water molecules.

The term "pharmaceutically acceptable" means that carriers, diluents, or additives are compatible with other ingredients in a formulation and are not harmful for recipients.

"Hepatocirrhosis" is a progressive hepatopathy which comprises wide suffer damage of liver parenchymal cell accompanied with reconstruct of hepatic lobule structure, causes often jaundie, portal hypeternsion, or hydroperitoneum, and finally hepatargy. Based on the experiments, the inventors of the present invention confirmed the elevated expression of type X sPLA$_2$ in pseudoacinus of hepatocytes derived from patient of hepatocirrhosis. Especially, the invention is useful for prevention or treatment of hepatocirrhosis.

In the present specification, the term "alkyl" employed alone or in combination with other terms means a straight- or branched chain monovalent hydrocarbon group having a specified number of carbon atoms. An example of the alkyl includes methyl, ethyl, n-propyl, isopropyl, n-butyl, isobutyl, sec-butyl, tert-butyl, n-pentyl, n-hexyl, n-heptyl, n-octyl, n-nonyl, n-decanyl, n-undecanyl, n-dodecanyl, n-tridecanyl, n-tetradecanyl, n-pentadecanyl, n-hexadecanyl, n-heptadecanyl, n-octadecanyl, n-nonadecanyl, n-eicosanyl and the like.

The term "alkenyl" employed alone or in combination with other terms in the present specification means a straight- or branched chain monovalent hydrocarbon group having a specified number of carbon atoms and at least one double bond. An example of the alkenyl includes vinyl, allyl, propenyl, crotonyl, isopentenyl, a variety of butenyl isomers and the like.

The term "alkynyl" used in the present specification means a straight or branched chain monovalent hydrocarbon group having a specified number of carbon atoms and at least one triple bond. The alkynyl may contain (a) double bond(s). An example of the alkynyl includes ethynyl, propynyl, 6-heptynyl, 7-octynyl, 8-nonynyl and the like.

The term "carbocyclic group" used in the present specification means a group derived from a saturated or unsaturated, substituted or unsubstituted 5 to 14 membered, preferably 5 to 10 membered, and more preferably 5 to 7 membered organic nucleus whose ring forming atoms (other than hydrogen atoms) are solely carbon atoms. A group containing two to three of the carbocyclic group is also included in the above stated group. An example of typical carbocyclic groups includes cycloalkyl such as cyclopropyl, cyclobutyl, cyclopentyl, cyclohexyl, cycloheptyl, and cyclooctyl, cycloalkenyl such as cyclobutylenyl, cyclopentenyl, cyclohexenyl, cycloheptenyl, and cyclooctenyl, phenyl, naphthyl, norbornyl, bicycloheptadienyl, indenyl, stilbenyl, terphenylyl, phenylcyclohexenyl, acenaphthyl, anthryl, biphenylyl, bibenzyl, and a phenylalkylphenyl derivative represented by the formula (II):

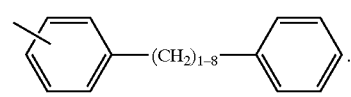

(II)

Phenyl, cycloalkyl or the like is preferred as a carbocyclic groups in the R$^3$ and R$^4$.

The term "heterocyclic group" used in the present specification means a group derived from monocyclic or polycyclic, saturated or unsaturated, substituted or unsubstituted heterocyclic nucleus having 5 to 14 ring atoms and containing 1 to 3 hetero atoms selected from the group consisting of nitrogen atom, oxygen atom, and sulfur atom. An example of the heterocyclic group includes pyridyl, pyrrolyl, furyl, benzofuryl, thienyl, benzothienyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, dibenzothiophenyl, indazolyl, imidazo[1,2-a]pyridinyl, benzotriazolyl, anthranilyl, 1,2-benzisoxazolyl, benzoxazolyl, benzothiazolyl, purinyl, puridinyl, dipyridinyl, phenylpyridinyl, benzylpyridinyl, pyrimidinyl, phenylpyrimidinyl, pyrazinyl, 1,3,5-triazinyl, quinolyl, phthalazinyl, quinazolinyl, quinoxalinyl, and the like.

Furyl, thienyl or the like is preferred as a heterocyclic group in the $R^3$ and $R^4$.

Preferred carbocyclic and heterocyclic groups in $R^5$ represented by the formula:

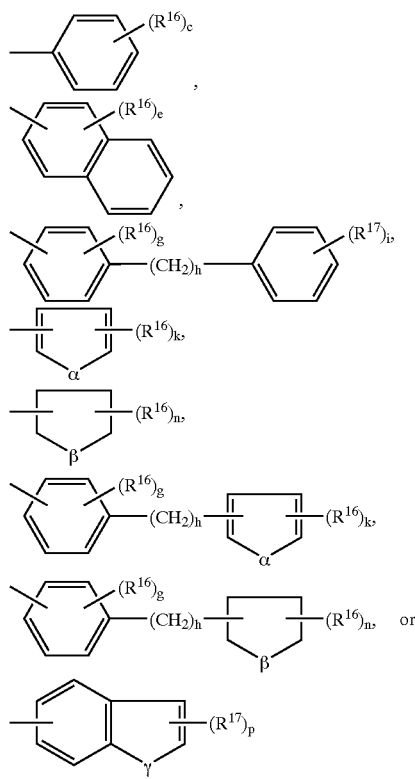

wherein h is an integer from 0 to 2, $R^{16}$ and $R^{17}$ are each independently halogen, C1–C10 alkyl, C1–C10 alkyloxy, C1–C10 alkylthio, aryloxy, or C1–C10 haloalkyl, α is oxygen atom or sulfur atom, β is —$CH_2$— or —$(CH_2)_2$—, γ is oxygen atom or sulfur atom, c, i, and p are each independently an integer from 0 to 5, e is an integer from 0 to 7, g is an integer from 0 to 4, k and n are each independently an integer from 0 to 3. When the above c, e, g, i, k, n, and/or p are 2 or more, a plural number of $R^{16}$ or $R^{17}$ may be different from one another. When $R^{16}$ is a substituent on the naphthyl group, the substituent may be substituted at any arbitrary position on the naphthyl group.

A more preferable example includes a group represented by the formula:

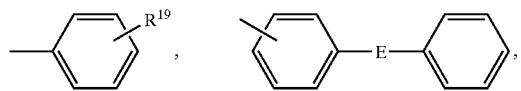

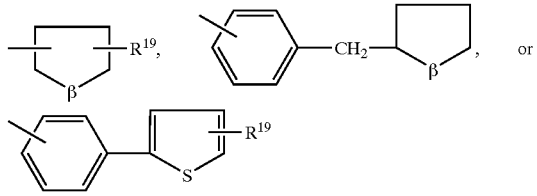

wherein $R^{19}$ is hydrogen atom, C1–C3 alkyl or halogen; E is a bond, —$CH_2$—, or —O—; β is —$CH_2$— or —$(CH_2)_2$— as defined above.

The above-mentioned "carbocyclic ring" C1–C3 alkyl and the above-mentioned "heterocyclic ring" C1–C3 alkyl, or the like is preferred as a group in the $R^5$.

The term "non-interfering substituent" in the present specification means a group suitable for substitution of the above mentioned "carbocyclic group", "heterocyclic group", and basic skeleton. An example of the non-interfering substituents includes C1–C10 alkyl, C2–C6 alkenyl, C2–C6 alkynyl, C7–C12 aralkyl such as benzyl and phenethyl, C7–C12 alkaryl, C3–C8 cycloalkyl, C3–C8 cycloalkenyl, phenyl, tolyl, xylyl, biphenylyl, C1–C10 alkyloxy, C1–C6 alkyloxy C1–C6 alkyl such as methyloxymethyl, ethyloxymethyl, methyloxyethyl, and ethyloxyethyl, C1–C6 alkyloxy C1–C6 alkyloxy such as methyloxymethyloxy and methyloxyethyloxy, C1–C6 alkylcarbonyl such as methylcarbonyl and ethylcarbonyl, C1–C6 alkylcarbonylamino such as methylcarbonylamino and ethylcarbonylamino, C1–C6 alkyloxyamino such as methyloxyamino and ethyloxyamino, C1–C6 alkyloxyaminocarbonyl such as methyloxyaminocarbonyl and ethyloxyaminocarbonyl, mono or di C1–C6 alkylamino such as methylamino, ethylamino, dimethylamino, and ethylmethylamino, C1–C10 alkylthio, C1–C6 alkylthiocarbonyl such as methylthiocarbonyl and ethylthiocarbonyl, C1–C6 alkylsulfinyl such as methylsulfinyl and ethylsulfinyl, C1–C6 alkylsulfonyl such as methylsulfonyl and ethylsulfonyl, C2–C6 haloalkyloxy such as 2-chloroethyloxy and 2-bromoethyloxy, C1–C6 haloalkylsulfonyl such as chloromethylsulfonyl and bromomethylsulfonyl, C1–C10 haloalkyl, C1–C6 hydroxyalkyl such as hydroxymethyl and hydroxyethyl, C1–C6 alkyloxycarbonyl such as methyloxycarbonyl and ethyloxycarbonyl, —$(CH_2)_{1-8}$—O—(C1–C6 alkyl), benzyloxy, aryloxy such as phenyloxy, arylthio such as phenylthio, —$(CONHSO_2R^{20})$ wherein $R^{20}$ is C1–C6 alkyl or aryl, —CHO, amino, amidino, halogen, carbamyl, carboxyl, carbalkoxy, —$(CH_2)_{1-8}$—COOH such as carboxymethyl, carboxyethyl, and carboxypropyl, cyano, cyanoguanidino, guanidino, hydrazide, hydrazino, hydroxy, hydroxyamino, nitro, phosphono, —$SO_3H$, thioacetal, thiocarbonyl, C1–C6 carbonyl, a carbocyclic group, a heterocyclic group and the like. These are optionally substituted with one or more substituents selected from the group consisting of C1–C6 alkyl, C1–C6 alkyloxy, C2–C6 haloalkyloxy, C1–C6 haloalkyl, and halogen.

Preferable are halogen, C1–C6 alkyl, C1–C6 alkyloxy, C1–C6 alkylthio, and C1–C6 haloalkyl as the "non-interfering substituent" of "substituted with non-interfering substituent" in the $R^3$, $R^4$, and $R^5$. More preferable are halogen, C1–C3 alkyl, C1–C3 alkyloxy, C1–C3 alkylthio, and C1–C3 haloalkyl.

Preferable are C1–C6 alkyl, aralkyl, C1–C6 alkyloxy, C1–C6 alkylthio, C1–C6 hydroxyalkyl, C2–C6 haloalkyloxy, halogen, carboxy, C1–C6 alkyloxycarbonyl, aryloxy, arylthio, a carbocyclic group, and a heterocyclic group as the "non-interfering substituent" in the $R^1$, $R^2$, $R^3$, $R^4$, and $R^7$. More preferable are C1–C6 alkyl, aralkyl, carboxy, C1–C6 hydroxyalkyl, phenyl, and C1–C6 alkyloxycarbonyl.

The term "halogen" in the present specification means fluorine, chlorine, bromine, and iodine.

The term "cycloalkyl" in the present specification means a monovalent cyclic hydrocarbon group having a specified number of carbon atoms. An example of the cycloalkyl includes cyclopropyl, cyclobutyl, cyclopentyl, cyclohexyl, cycloheptyl, cyclooctyl and the like.

The term "cycloalkenyl" in the present specification means a monovalent cyclic hydrocarbon group having a specified number of carbon atoms and at least one double bond(s). An example of the cycloalkenyl includes 1-cyclopropenyl, 2-cyclopropenyl, 1-cyclobutenyl, 2-cyclobutenyl and the like.

In the present specification, an example of "alkyloxy" includes methyloxy, ethyloxy, n-propyloxy, isopropyloxy, n-butyloxy, n-pentyloxy, n-hexyloxy and the like.

In the present specification, an example of "alkylthio" includes methylthio, ethylthio, n-propylthio, isopropylthio, n-butylthio, n-pentylthio, n-hexylthio and the like.

The term "acidic group" in the present specification means an organic group functioning as a proton donor capable of hydrogen bonding when attached to a basic skeleton through a suitable linking atom (hereinafter defined as "acid linker"). An example of the acidic group includes a group represented by the formula:

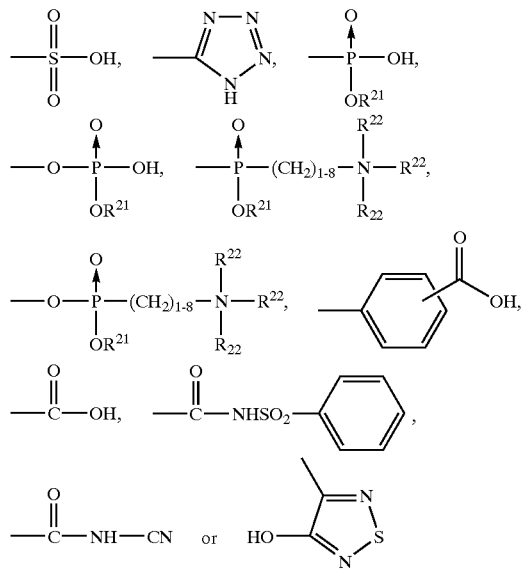

wherein $R^{21}$ is hydrogen atom, a metal, or C1–C10 alkyl; each $R^{22}$ is independently hydrogen atom or C1–C10 alkyl, provided that at least one of $R^{21}$ or $R^{22}$ is hydrogen atom in case of an acidic group having both $R^{21}$ and $R^{22}$. Preferable is —COOH, —SO$_3$H, —CONHSO$_2$C$_6$H$_5$, or P(O)(OH)$_2$. More preferable is —COOH.

The term "acid linker" in the present specification means a divalent linking group represented by a symbol -($L^1$)-, and it functions to join a basic skeleton to an "acidic group" in the general relationship. An example of it includes a group represented by the formula:

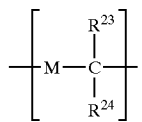

wherein M is —CH$_2$—, —O—, —N($R^{25}$)—, or —S— wherein $R^{23}$ and $R^{24}$ are each independently hydrogen atom, C1–C10 alkyl, aryl, aralkyl, carboxy, or halogens and a group represented by the formula:

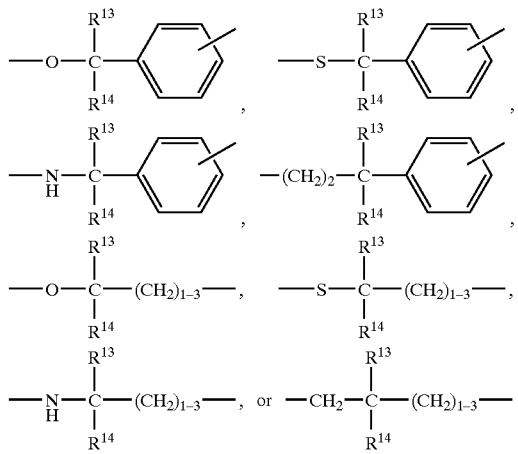

wherein $R^{13}$ and $R^{14}$ are each independently hydrogen atom, C1–C10 alkyl, C1–C10 aralkyl, carboxy, alkyloxycarbonyl, or halogen. Preferable are —O—CH$_2$—, —S—CH$_2$—, —N($R^{25}$)—CH$_2$—, —CH$_2$—CH$_2$—, —O—CH(CH$_3$)—, or —O—CH((CH$_2$)$_2$C$_6$H$_5$)— wherein $R^{25}$ is C1–C6 alkyl. More preferable is —O—CH$_2$— or —S—CH$_2$—.

In the present specification, the term "acid linker length" means the number of atoms (except for hydrogen atoms) in the shortest chain of a linking group -($L^1$)- which connects a basic skeleton with the "acidic group". The presence of a carbocyclic ring in -($L^1$)- counts as the number of atoms approximately equivalent to the calculated diameter of the carbocyclic ring. Thus, a benzene and cyclohexane ring in the acid linker counts as two atoms in calculating the length of -($L^1$)-. A preferable length is 2 to 3.

The term "haloalkyl" in the present specification means the aforementioned "alkyl" substituted with the aforementioned "halogen" at arbitrary position(s). An example of the haloalkyl includes chloromethyl, trifluoromethyl, 2-chloromethyl, 2-bromomethyl and the like.

The term "hydroxyalkyl" in the present specification means the aforementioned "alkyl" substituted with hydroxy at arbitrary position(s). An example of the hydroxyalkyl includes hydroxymethyl, 2-hydroxyethyl, 3-hydroxypropyl and the like. In this case, hydroxymethyl is preferable.

In the present specification, the term "haloalkyl" in "haloalkyloxy" is the same as defined above. An example of it includes 2-chloroethyloxy, 2-trifluoroethyloxy, 2-chloroethyloxy and the like.

The term "aryl" in the present specification means a monocyclic or condensed cyclic aromatic hydrocarbon. An example of the aryl includes phenyl, 1-naphthyl, 2-naphthyl, anthryl and the like. Particularly, phenyl and 1-naphthyl are preferred.

The term "aralkyl" in the present specification means a group wherein the aforementioned "alkyl" is substituted with the above-mentioned "aryl". Such aryl may have a bond at any substitutable position. An example of it includes benzyl, phenethyl, phenylpropyl such as 3-phenylpropyl, naphthylmethyl such as 1-naphthylmethyl and the like.

An example of the "alkyloxycarbonyl" in the present specification includes methyloxycarbonyl, ethyloxycarbonyl, n-propyloxycarbonyl and the like.

An example of the "aryloxy" in the present specification includes phenyloxy and the like.

An example of the "arylthio" in the present specification includes phenylthio and the like.

The term "halophenyl" in the present specification means phenyl substituted with the aforementioned "halogen" at one or more position(s). An example of the halophenyl includes fluorophenyl, chlorophenyl, bromophenyl, iodophenyl, difluorophenyl, dichlorophenyl, dibromophenyl, trifluorophenyl, trichlorophenyl, tribromophenyl, chlorofluorophenyl, bromochlorophenyl, and the like.

The term "cyclohexene ring" of D ring in the present specification means a cyclohexene ring having only one double bond at the condensation part with the adjacent ring.

Preferable combinations of "A ring" and "—B—" are represented by the following (m)–(r):

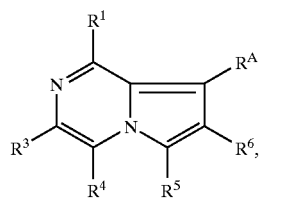
(m)

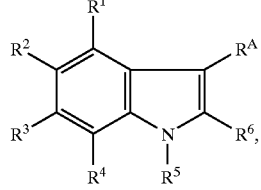
(n)

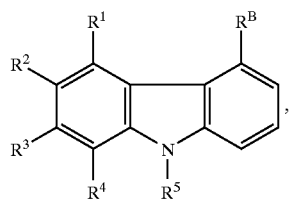
(o)

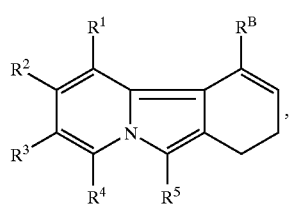
(p)

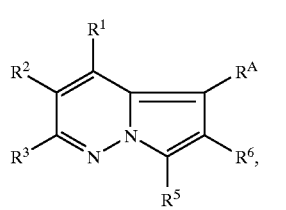
(q) or

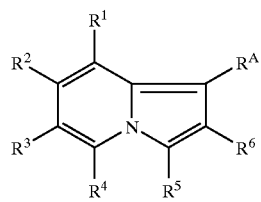
(r)

Particularly, combinations represented by (m)–(p) are preferred.

Furthermore, compounds represented by formula (1) to (19) are most preferred.

BEST MODE FOR CARRYING OUT THE INVENTION

The present invention relates to the prevention or treatment of Alzheimer's disease by a type-X sPLA$_2$ inhibitor. The type-X sPLA$_2$ inhibitor may be known one and selected from sPLA2 inhibitors, for example, compounds described in EP-620214 (JP Laid-Open (Tokukai) No. 95/010838, U.S. Pat. No. 5,578,634), EP-620215 (JP Laid-Open (Tokukai) No. 95/025850, U.S. Pat. No. 5,684,034), EP-675110 (JP Laid-Open (Tokukai) No. 95/285933, U.S. Pat. No. 5,654,326), WO 96/03120 (JP Laid-Open No. 98/505336), WO 96/03376 (JP Laid-Open No. 98/503208, U.S. Pat. No. 5,641,800), WO 96/03383 (JP Laid-Open No. 98/505584), WO 97/21664 (EP-779271), WO 97/21716 (EP-779273), WO 98/18464 (EP839806), WO98/24437 (EP846687), WO98/24756, WO98/24794, WO98/25609, WO99/51605, WO99/59999 and the like, or parabromophenacyl-bromide, mepacrine, manoalide, thielocin A$_1$ and the like.

As another type-X sPLA$_2$ inhibitor, can be used the compounds represented in PCT/JP00/07024 by the formula:

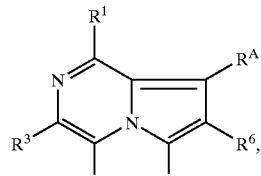

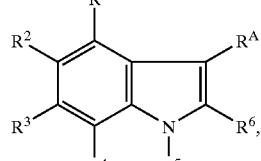

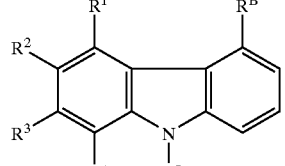

wherein R$^1$, R$^2$, R$^3$, and R$^4$ are each independently hydrogen atom, a non-interfering substituent(s) and the like, R$^5$ is carbocyclic groups, heterocyclic groups, R$^6$ is hydrogen atom, C1–C3 alkyl and the like, R$^A$ is —COCONH$_2$ and the like, R$^B$ is —CONH$_2$, and the like.

Further, compounds identified as type-X sPLA$_2$ inhibitors by the following procedure and the like may be used in the present invention. The effect as the composition of the present invention is examined as follows.

At first, a cell expressing human type-X sPLA$_2$ is prepared. That is, cDNA sequence encoding human type-X sPLA$_2$ (Cupillard et al., J. Biol. Chem, 1997, 272, 15745–15752) is inserted into an expression vector for mammalian cells. The obtained expression vector is transfected into the host cell and the cell stably expressing human type-X sPLA$_2$ is obtained. The transfected cell is cultured in medium and its culture supernatant is used for the measurement of each enzyme activity.

(Inhibition Test)

In order to identify and evaluate an inhibitor of type-X sPLA$_2$, the following chromogenic assay is utilized. A general explanation for this assay is described in "Analysis of Human Synovial Fluid Phospholipase A$_2$ on Short Chain Phosphatidylcholine-Mixed Micelles: Development of a Spectrophotometric Assay Suitable for a Micortiterplate Reader" (Analytical Biochemistry, 204, pp 190–197, 1992 by Laure. J. Reynolds. Lori L. Hughes and Edward A. Dennis.

Several kinds of the compounds represented by the formula (I) can be synthesized in accordance with the methods described in PCT/JP00/07024, EP-620214 (JP Laid-Open (Tokukai) No. 95/010838, U.S. Pat. No. 5,578,634), EP-620215 (JP Laid-Open (Tokukai) No. 95/025850, U.S. Pat. No. 5,684,034), EP-675110 (JP Laid-Open (Tokukai) No. 95/285933, U.S. Pat. No. 5,654,326), WO 96/03120 (JP Laid-Open No. 98/505336), WO 96/03383 (JP Laid-Open No. 98/505584), WO 98/18464 (EP839806), WO99/51605, WO99/59999 and the like.

The composition for treatment or prevention in the present invention may be administered to a patient through a variety of routes including oral, aerosol, rectal, percutaneous, subcutaneous, intravenous, intramuscular, and nasal routes. A formulation according to the present invention may be manufactured by combining (for example, admixing) a curatively effective amount of a compound of the present invention with a pharmaceutically acceptable carrier or diluent. The formulation of the present invention may be manufactured with the use of well-known and easily available ingredients in accordance with a known method.

In case of manufacturing a composition of the present invention, active ingredients are admixed, or diluted with a carrier, or they are contained in a carrier in the form of capsule, sacheier, paper, or another container. In case of functioning a carrier as a diluent, the carrier is a solid, semi-solid, or liquid material which functions as a medium. Accordingly, a formulation according to the present invention may be produced in the form of tablet, pill, powder medicine, intraoral medicine, elixir agent, suspending agent, emulsifier, dissolving agent, syrup agent, aerosol agent (solid in liquid medium), and ointment. Such a formulation may contain up to 10% of an active compound. It is preferred to formulate a compound having activities for the treatment or prevention of hepatocirrhosis prior to administration.

Any suitable carrier well known to those skilled in the art may be used for the formulation. In such formulation, a carrier is in the form of solid, liquid, or a mixture thereof. For instance, a compound having type-X sPLA$_2$ inhibitory activities is dissolved into 4% dextrose/0.5% sodium citrate aqueous solution so as to be 2 mg/mL concentration for intravenous injection. Solid formulation includes powder, tablet, and capsule. Solid carrier consists of one or more of material(s) for serving also as fragrant, lubricant, dissolving agent, suspension, binder, tablet disintegrator, capsule. A tablet for oral administration contains a suitable excipient such as calcium carbonate, sodium carbonate, lactose, calcium phosphate and the like together with a disintegrator such as corn starch, alginic acid and the like and/or a binder such as gelatin, acacia and the like, and a lubricant such as magnesium stearate, stearic acid, talc and the like.

In a powder medicine, a carrier is a finely pulverized solid which is blended with finely pulverized active ingredients. In a tablet, active ingredients are admixed with a carrier having required binding power in a suitable ratio, and it is solidified in a desired shape and size. Powder medicine and tablet contain about 1 to about 99% by weight of the active ingredients being novel compounds according to the present invention. An example of suitable solid carriers includes magnesium carbonate, magnesium stearate, talc, sugar, lactose, pectin, dextrin, starch, gelatin, tragacanth gum, methyl cellulose, sodium carboxymethylcellulose, low-melting wax, and cocoa butter.

An axenic liquid formulation contains suspending agent, emulsifier, syrup agent, and elixir agent. Active ingredients may be dissolved or suspended into a pharmaceutically acceptable carrier such as sterile water, a sterile organic solvent, a mixture thereof and the like. Active ingredients may be dissolved frequently into a suitable organic solvent such as propylene glycol aqueous solution. When finely pulverized active ingredients are dispersed into aqueous starch, sodium carboxymethylcellulose solution, or suitable oil, the other compositions can be prepared.

The dosage varies with the conditions of the disease, administration route, age and body weight of patient. In the case of intravenous administration, the dosage can generally be between 0.01 to 10 mg/kg/h for adult, preferably 0.1 to 1 mg/kg/h.

EXAMPLE

Example 1

Preparation of Cells Expressing Human Type-X sPLA$_2$ and Their Culture Supernatants cDNA sequence encoding human type-X sPLA$_2$ (Cupillard et al., J. Biol. Chem, 1997, 272, 15745–15752) was inserted into the downstream region of the promoter of pSVL SV40 Late Promoter Expression Vector (Amersham Pharmacia Biotech Inc.) that is an expression vector for mammalian cells. The obtained expression vector was transfected into the host CHO cells with a LipofectAMINE reagent (Gibco BRL Inc.) according to the manufacture's instruction to obtain the CHO cells stably expressing human type-X sPLA$_2$. The transfected cell was cultured in α-MEM medium containing 10% fetal calf serum for 3 days and its culture supernatant was used for the measurement of each enzyme activity.

Example 2

Inhibition Test

In order to identify and evaluate an inhibitor of type-X sPLA$_2$, the following chromogenic assay is utilized. This assay has been applied for high volume screening using a 96-well microtiterplate. A general explanation for this assay is described in "Analysis of Human Synovial Fluid Phospholipase A$_2$ on Short Chain Phosphatidylcholine-Mixed Micelles: Development of a Spectrophotometric Assay Suitable for a Micortiterplate Reader" (Analytical Biochemistry, 204, pp 190–197, 1992 by Laure. J. Reynolds. Lori L. Hughes and Edward A. Dennis.

Test compounds (or solvent blank) were added according to the alignment of plates that had been previously set. Human type-X sPLA$_2$ was incubated (30 min at 40° C. (15 µl/well)) with diheptanoylthio PC (1 mM) in the presence of Triton X-100 (0.3 mM) and 5,5'-dithiobis(2-nitrobenzoic acid) (125 µM) in Tris-HCl buffer (25 mM, pH 7.5) containing CaCl$_2$ (10 mM), KCl (100 mM), and bovine serum albumin (1.0 mg/mL). The changes in the absorbance at 405 nm were measured and the inhibition activities were calculated.

The IC$_{50}$ value was determined by plotting the log concentration of the above-mentioned compounds (1)–(19) with respect to their inhibition values within 10% to 90% inhibitory range.

Results of the type-X sPLA$_2$ inhibition test is shown in the following Table 1.

TABLE 1

| Compound No. | IC$_{50}$(nM) | Compound No. | IC$_{50}$(nM) |
|---|---|---|---|
| 1 | 10 | 11 | 10 |
| 2 | 10 | 12 | 16 |
| 3 | 5 | 13 | 19 |
| 4 | 27 | 14 | 9 |
| 5 | 12 | 15 | 17 |
| 6 | 17 | 16 | 7 |
| 7 | 5 | 17 | 12 |
| 8 | 3 | 18 | 16 |
| 9 | 13 | 19 | 26 |
| 10 | 12 | | |

Example 3

Immunohistochemical Analysis in Human Hepatocirrhosis Tissues with Anti-type-X sPLA$_2$ Antibody In this experiment, anti-type-X sPLA$_2$ antibody which was described in "The Journal of Biological Chemistry Vol. 274, No. 48, pp. 34203–34211 1999" was used. Paraffin embedded preparations of human liver cirrhosis tissues and corresponding normal tissues were purchased from Biochain Inc. (San Leandro, Calif.). The tissue sections in the slides were dewaxed, treated in methanol containing 0.3% H$_2$O$_2$ for 30 min to remove the endogenous peroxidase activity and incubated with 5% normal goat serum for 20 min. The slides were then incubated with anti-type sPLA$_2$ antibody (6 µg/mL) in PBS containing 0.1% bovine serum albumin for 14 hr at 4° C. After washing with PBS, they were incubated with biotin-conjugated goat anti-rabbit IgG antibody for 30 min followed by treatment with peroxidase labelled avidin-biotin complex reagent (Vector Laboratories). After washing, the samples were processed with 200 µg/ml diaminobenzidine hydrochloride substrate dissolved in 50 mmol/L Tris-HCl (pH 7.6) containing 0.006% H$_2$O$_2$ for 10 min resulting in the appearance of color dependent on the peroxidase activity to visualize the type-X sPLA$_2$ expression in the tissue preparations. In addition, the nuclei were counterstained with 0.4% hematoxylin solution. Positive signals representative for type-X sPLA$_2$ expression was visualized as a dark-brownish color of diaminobenzidine deposit. The neutralization of type-X sPLA$_2$ specific signals was conducted by incubating anti-type-X sPLA$_2$ antibody with purified type-X sPLA$_2$ protein (60 µg/ml) for 2 hr before the addition to the slides.

Consequently, positive signals representative for type-X sPLA$_2$ expression were weakly observed in hepatic lobule and Kupffer's satellate cells in normal human liver tissues. In contrast, the positive signals were strongly detected in the hepatocytes of pseudolobule in the liver prepared from patients of hepatocirrhosis. Since the addition of type-X sPLA$_2$ protein resulted in abolishment of the signals, they were verified as the specific signals for type-X sPLA$_2$. In addition, there was no positive signal when IgG prepared from non-immunized rabbit was used. Taken together, these findings suggest that the expression of type-X sPLA$_2$ protein was greatly elevated in human liver cirrhosis tissues.

FORMULATION EXAMPLE

It is to be noted that the following Formulation Examples 1 to 8 are mere illustration, but not intended to limit the scope of the invention. The term "active ingredient" means the compounds having an anti-hepatocirrhosis activity, the prodrugs thereof, their pharmaceutical acceptable salts, or their hydrate.

Formulation Example 1

Hard gelatin capsules are prepared using of the following ingredients:

| | Dose (mg/capsule) |
|---|---|
| Active ingredient | 250 |
| Starch, dried | 200 |
| Magnesium stearate | 10 |
| Total | 460 mg |

Formulation Example 2

A tablet is prepared using of the following ingredients:

| | Dose (mg/tablet) |
|---|---|
| Active ingredient | 250 |
| Cellulose, microcrystals | 400 |
| Silicon dioxide, fumed | 10 |
| Stearic acid | 5 |
| Total | 665 mg |

The components are blended and compressed to form tablets each weighing 665 mg.

Formulation Example 3

An aerosol solution is prepared containing the following components:

| | Weight |
|---|---|
| Active ingredient | 0.25 |
| Ethanol | 25.75 |
| Propellant 22 (chlorodifluoromethane) | 74.00 |
| Total | 100.00 |

The active compound is mixed with ethanol and the admixture added to a portion of the propellant 22, cooled to −30° C. and transferred to filling device. The required amount is then fed to stainless steel container and diluted with the reminder of the propellant. The valve units are then fitted to the container.

Formulation Example 4

Tablets, each containing 60 mg of active ingredient, are made as follows.

| Active ingredient | 60 mg |
|---|---|
| Starch | 45 mg |
| Microcrystals cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve, and the mixed thoroughly. The aqueous solution containing polyvinylpyrrolidone is mixed with the resultant powder, and the admixture then is passed through a No. 14 mesh U.S. sieve. The granules so produced are dried at 50° C. and passed through a No. 18 mesh U.S. sieve. The sodium carboxymethyl starch, magnesium stearate, and talc, previously passed through No. 60 mesh U.S. sieve, are then added to the granules which, after mixing, are compressed on a tablet machine to yield tablets each weighing 150 mg.

Formulation Example 5

Capsules, each containing 80 mg of active ingredient, are made as follows:

| Active ingredient | 80 mg |
|---|---|
| Starch | 59 mg |
| Microcrystals cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation Example 6

Suppository, each containing 225 mg of active ingredient, are made as follows:

| Active ingredient | 225 mg |
|---|---|
| Saturated fatty acid glycerides | 2000 mg |
| Total | 2225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation Example 7

Suspensions, each containing 50 mg of active ingredient per 5 mL dose, are made as follows:

| Active ingredient | 50 mg |
|---|---|
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 U.S. sieve, and mixed with the sodium carboxymethyl cellulose and syrup to form a smooth paste. The benzoic acid solution and flavor are diluted with a portion of the water and added, with stirring. Sufficient water is then added to produce the required volume.

Formulation Example 8

An intravenous formulation may be prepared as follows:

| Active ingredient | 100 mg |
|---|---|
| Saturated fatty acid glycerides | 1000 mL |

The solution of the above ingredients generally is administered intravenously to a subject at a rate of 1 mL per minute.

INDUSTRIAL APPLICABILITY

It is provided that type-X sPLA$_2$ inhibitors are useful in preventing or treating hepatocirrhosis.

What is claimed is:
1. A method of treating a mammal, including a human, to alleviate the pathological effects of hepatocirrhosis, which comprises administering to said mammal a pharmaceutically effective amount of a compound represented by the formula (I):

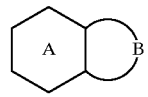

(I)

wherein Ring A is represented by the formula (a) to (d):

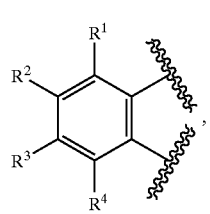

(a)

(b)

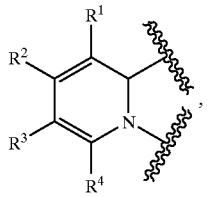

(c)

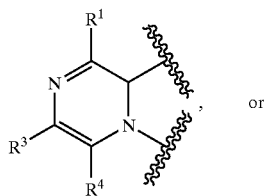  or (d)

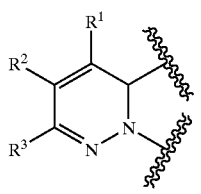

wherein $R^1$ and $R^2$ are each independently hydrogen atom, non-interfering substituent, or -($L^1$)-(acidic group) wherein $L^1$ is an acid linker having an acid linker length of 1 to 5, provided that one of the $R^1$ and $R^2$ is -($L^1$)-(acidic group);

$R^3$ and $R^4$ are each independently hydrogen atom, non-interfering substituent, carbocyclic group, carbocyclic group substituted with a non-interfering substituent(s), heterocyclic group, or heterocyclic group substituted by a non-interfering substituent(s); and —B— is represented by the formula (e) to (h):

(e)

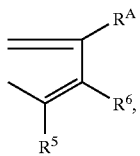

(f)

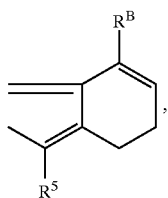

(g)

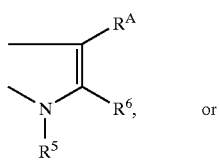  or (h)

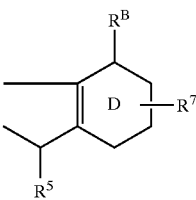

wherein $R^5$ is (j) C1 to C20 alkyl, C2 to C20 alkenyl, C2 to C20 alkynyl, carbocyclic group, or heterocyclic group, (k) the group represented by (j) each substituted independently with at least one group selected from non-interfering substituents, or -($L^2$)-$R^8$ wherein $L^2$ is a divalent linking group of 1 to 18 atom(s) selected from hydrogen atom(s), nitrogen atom(s), carbon atom(s), oxygen atom(s), and sulfur atom(s), and $R^8$ is a group selected from the groups (j) and (k);

$R^6$ is hydrogen atom, halogen, C1 to C3 alkyl, C3 to C4 cycloalkyl, C3 to C4 cycloalkenyl, C1 to C3 alkyloxy, or C1 to C3 alkylthio;

$R^7$ is hydrogen atom or non-interfering substituent;

$R^A$ is represented by the formula:

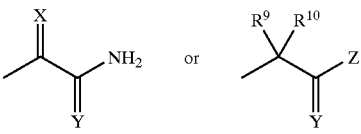

wherein $R^9$ and $R^{10}$ are each independently hydrogen atom, C1 to C3 alkyl, or halogen;

X and Y are each independently oxygen atom or sulfur atom; and

Z is —$NH_2$ or —$NHNH_2$;

$R^B$ is —$CONH_2$ or —$CONHNH_2$; and,

Ring D is cyclohexene ring or benzene ring;

provided that Ring A is (b), (c), or (d) when —B— is (e) or (f), a prodrug thereof, its pharmaceutically acceptable salt, or its solvate, together with a pharmaceutically acceptable carrier diluent or additive.

2. The method of claim 1, wherein $R^1$ is hydrogen atom or -($L^3$)-$R^{11}$ wherein $L^3$ is —$OCH_2$—, —$SCH_2$—, —NH—$CH_2$—, —$CH_2$—$CH_2$—, —O—$CH(CH_3)$—, or —O—CH($CH_2CH_2C_6H_5$)—; $R^{11}$ is —COOH, —$CONHSO_2C_6H_5$, —$SO_3H$, or —$P(O)(OH)_2$, and $R^2$ is hydrogen atom or -($L^4$)-$R^{12}$ wherein $L^4$ is represented by the formula:

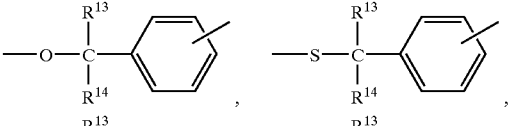

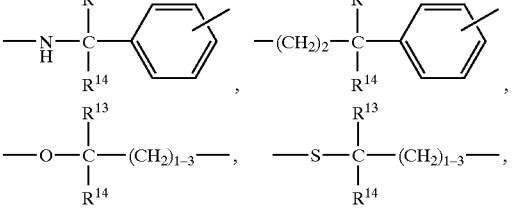

-continued

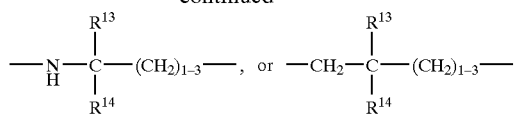

wherein $R^{13}$ and $R^{14}$ are each independently hydrogen atom, C1 to C10 alkyl, C1 to C10 aralkyl, carboxy, alkyloxycarbonyl, or halogen; $R^{12}$ is —COOH, —SO$_3$H, or —P(O)(OH)$_2$, provided $R^1$ and $R^2$ are not hydrogen atom at the same time.

3. The method of claim 1, wherein $R^3$ is hydrogen atom, C1 to C6 alkyl, C3 to C6 cycloalkyl, aryl, or a heterocyclic group and $R^4$ is hydrogen atom or halogen.

4. The method of claim 1, wherein $R^5$ is —(CH$_2$)$_{1-6}$—$R^{15}$ wherein $R^{15}$ is represented by the formula:

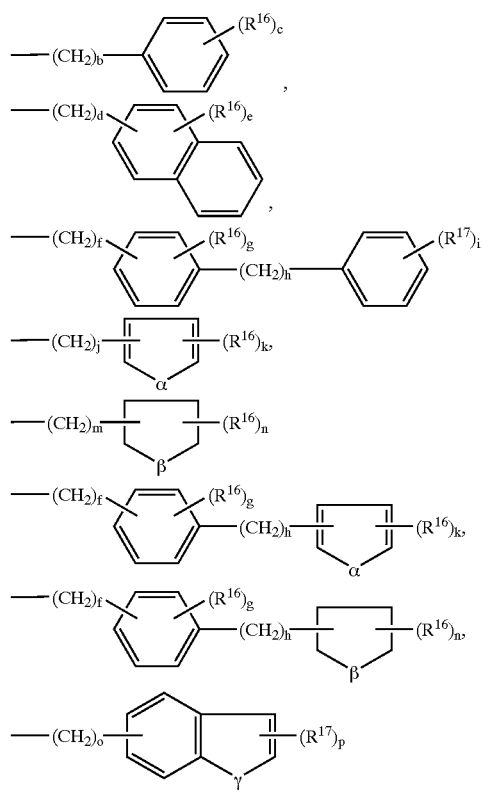

wherein b, d, f, h, j, m, and o are independently an integer from 0 to 2; $R^{16}$ and $R^{17}$ are each independently halogen, C1 to C10 alkyl, C1 to C10 alkyloxy, C1 to C10 alkylthio, aryloxy, or C1 to C10 haloalkyl; α is oxygen atom or sulfur atom; β is —CH$_2$— or —(CH$_2$)$_2$—; γ is oxygen atom or sulfur atom; c, i, and p are independently an integer from 0 to 5; e is an integer from 0 to 7; g is an integer from 0 to 4; k and n are each independently an integer from 0 to 3.

5. The method of claim 4, wherein $R^5$ is —CH$_2$—$R^{18}$ wherein $R^{18}$ is represented by the formula:

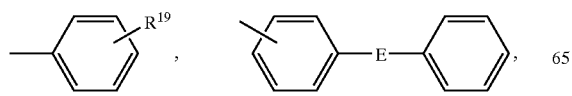

-continued

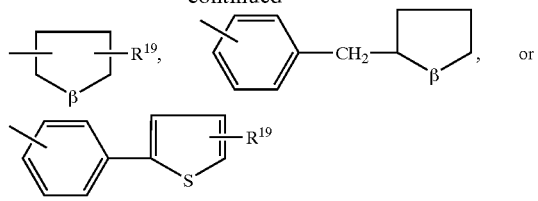

wherein β is —CH$_2$— or —(CH$_2$)$_2$—; $R^{19}$ is hydrogen atom, C1 to C3 alkyl, or halogen; E is a bond, —CH$_2$— or —O—.

6. The method of claim 1, wherein $R^1$ is —OCH$_2$COOH.

7. The method of claim 1, wherein $R^2$ is hydrogen atom.

8. The method of claim 1, wherein $R^6$ is C1 to C3 alkyl.

9. The method of claim 1, wherein $R^A$ is —CH$_2$CONH$_2$ or —COCONH$_2$.

10. A method of treating a mammal, including a human, to alleviate the pathological effects of hepatocirrhosis, which comprises administering to said mammal a pharmaceutically effective amount of a compound represented by the formula:

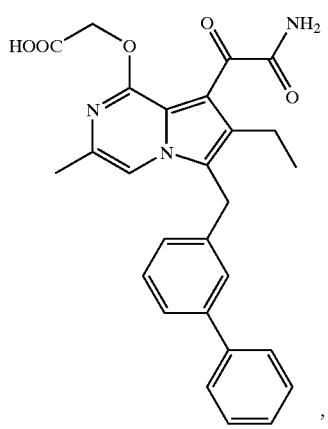

(1)

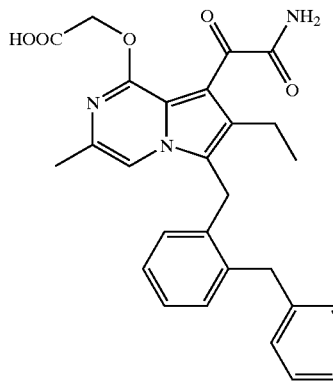

(2)

(3) 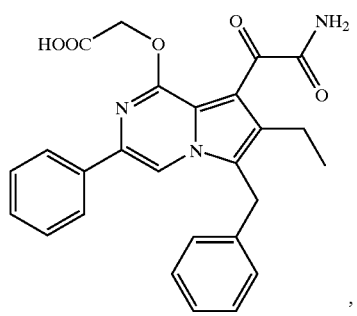
(4) 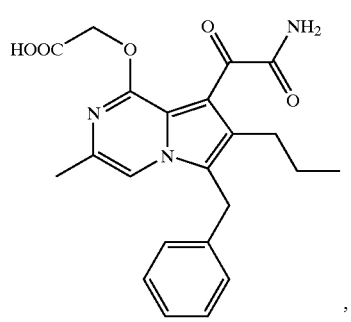
(5) 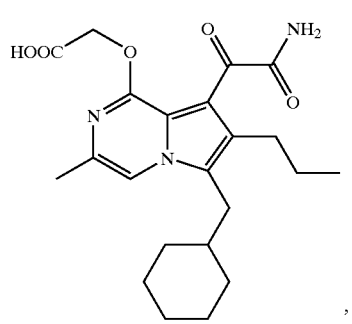
(6) 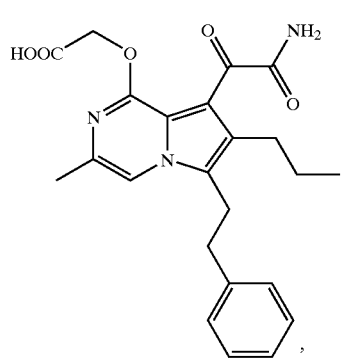
(7) 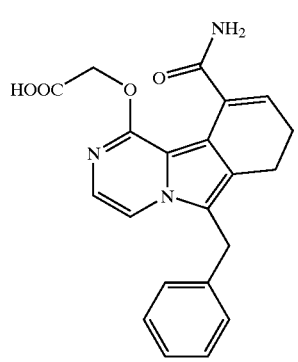
(8) 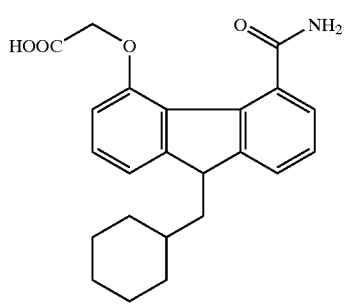
(9) 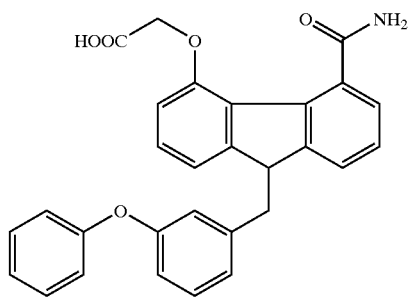
(10) 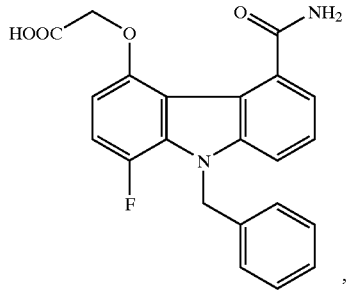
(11) 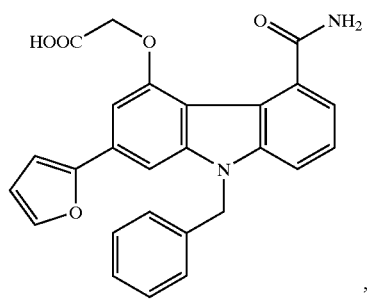
(12) 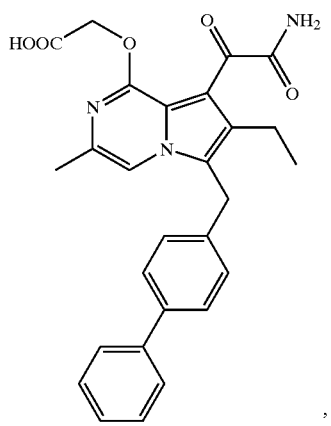

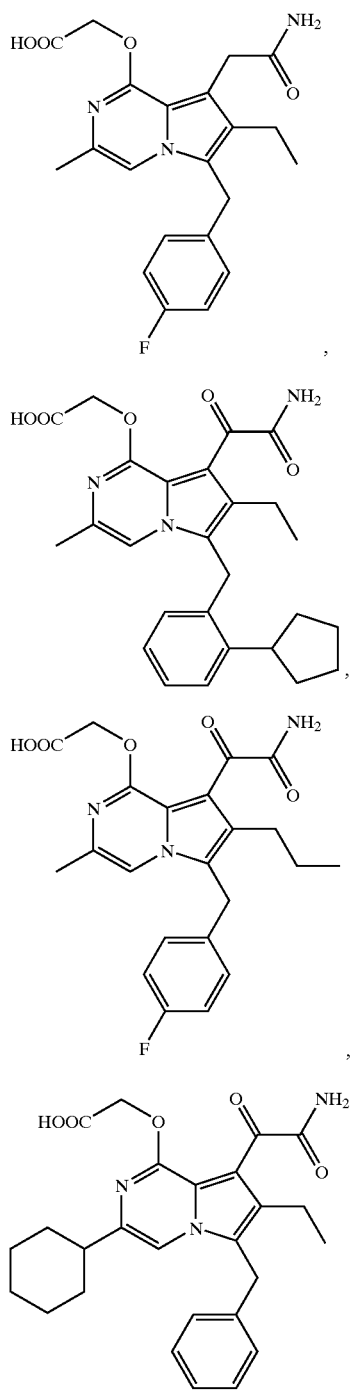
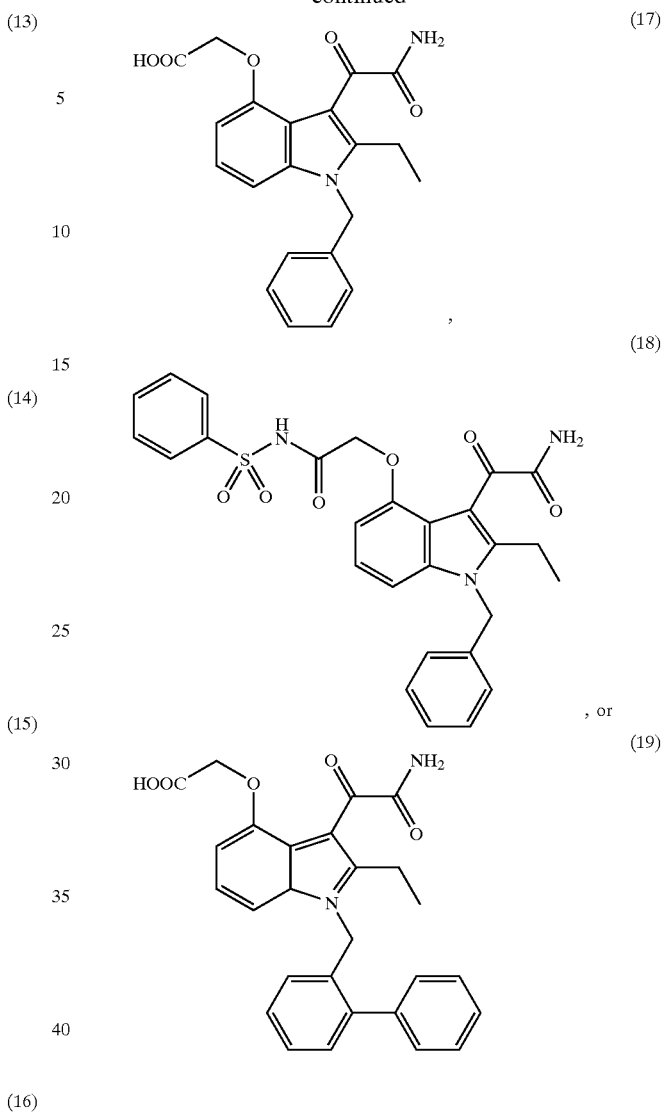
a prodrug thereof, its pharmaceutically acceptable salt, or its solvate.
11. A method of treating a mammal, including a human, to alleviate the pathological effects of hepatocirrhosis, which comprises administering to said mammal a type-X sPLA$_2$ inhibitor in a pharmaceutically effective amount.
* * * * *